United States Patent
Engelbart et al.

(10) Patent No.: US 8,068,659 B2
(45) Date of Patent: Nov. 29, 2011

(54) METHOD AND SYSTEM FOR DETERMINING CUMULATIVE FOREIGN OBJECT CHARACTERISTICS DURING FABRICATION OF A COMPOSITE STRUCTURE

(75) Inventors: Roger W. Engelbart, St. Louis, MO (US); Reed Edward Hannebaum, Belleville, IL (US)

(73) Assignee: The Boeing Company, Chicago, IL (US)

( * ) Notice: Subject to any disclaimer, the term of this patent is extended or adjusted under 35 U.S.C. 154(b) by 1034 days.

(21) Appl. No.: 11/927,115

(22) Filed: Oct. 29, 2007

(65) Prior Publication Data

US 2009/0148030 A1 Jun. 11, 2009

Related U.S. Application Data

(63) Continuation-in-part of application No. 10/726,099, filed on Dec. 2, 2003, now Pat. No. 7,289,656.

(51) Int. Cl.
*G06K 9/00* (2006.01)

(52) U.S. Cl. .......................................... 382/141; 700/110

(58) Field of Classification Search .................. 382/141; 348/86, 92; 700/109, 110
See application file for complete search history.

(56) References Cited

U.S. PATENT DOCUMENTS

| | | | |
|---|---|---|---|
| 4,223,346 A | | 9/1980 | Neiheisel et al. |
| 4,507,564 A | | 3/1985 | Shimada |
| 5,963,660 A | * | 10/1999 | Koontz et al. ............... 382/141 |
| 6,064,429 A | * | 5/2000 | Belk et al. .................. 348/128 |
| 6,799,619 B2 | | 10/2004 | Holmes et al. |
| 6,814,822 B2 | | 11/2004 | Holmes et al. |
| 6,871,684 B2 | | 3/2005 | Engelbart et al. |
| 7,039,485 B2 | | 5/2006 | Engelbart et al. |
| 7,171,033 B2 | | 1/2007 | Engelbart et al. |
| 7,193,696 B2 | | 3/2007 | Engelbart et al. |
| 7,236,625 B2 | | 6/2007 | Engelbart et al. |
| 2002/0141632 A1 | * | 10/2002 | Engelbart et al. ............ 382/141 |
| 2002/0176617 A1 | | 11/2002 | Simonetti |
| 2005/0025350 A1 | | 2/2005 | Engelbart et al. |
| 2005/0047643 A1 | * | 3/2005 | Lowe .......................... 382/141 |
| 2005/0117793 A1 | | 6/2005 | Engelbart et al. |
| 2005/0203657 A1 | | 9/2005 | Engelbart et al. |
| 2006/0108048 A1 | | 5/2006 | Engelbart et al. |
| 2006/0109454 A1 | | 5/2006 | Engelbart et al. |
| 2006/0152712 A1 | | 7/2006 | Engelbart et al. |
| 2006/0191622 A1 | | 8/2006 | Ritter et al. |
| 2007/0034313 A1 | | 2/2007 | Engelbart et al. |
| 2007/0096019 A1 | | 5/2007 | Engelbart et al. |
| 2007/0097359 A1 | | 5/2007 | Engelbart et al. |
| 2007/0173966 A1 | * | 7/2007 | Oldani ......................... 700/110 |
| 2007/0229805 A1 | | 10/2007 | Engelbart et al. |

FOREIGN PATENT DOCUMENTS

WO 2007078408 A2 12/2007

OTHER PUBLICATIONS

USPTO Office Action for U.S. Appl. No. 12/813,329 dated Feb. 4, 2011.

* cited by examiner

*Primary Examiner* — Jon Chang
(74) *Attorney, Agent, or Firm* — Yee & Associates, P.C.

(57) ABSTRACT

Method and system for determining cumulative foreign object characteristics during fabrication of a composite structure. Images of sequential segments of a composite structure may be recorded during placement of the composite structure. The recorded images may be analyzed for detecting foreign objects on the composite structure. Cumulative foreign object characteristics of the foreign objects detected on the composite structure may be determined, and the cumulative foreign object characteristics may be provided to a user.

19 Claims, 7 Drawing Sheets

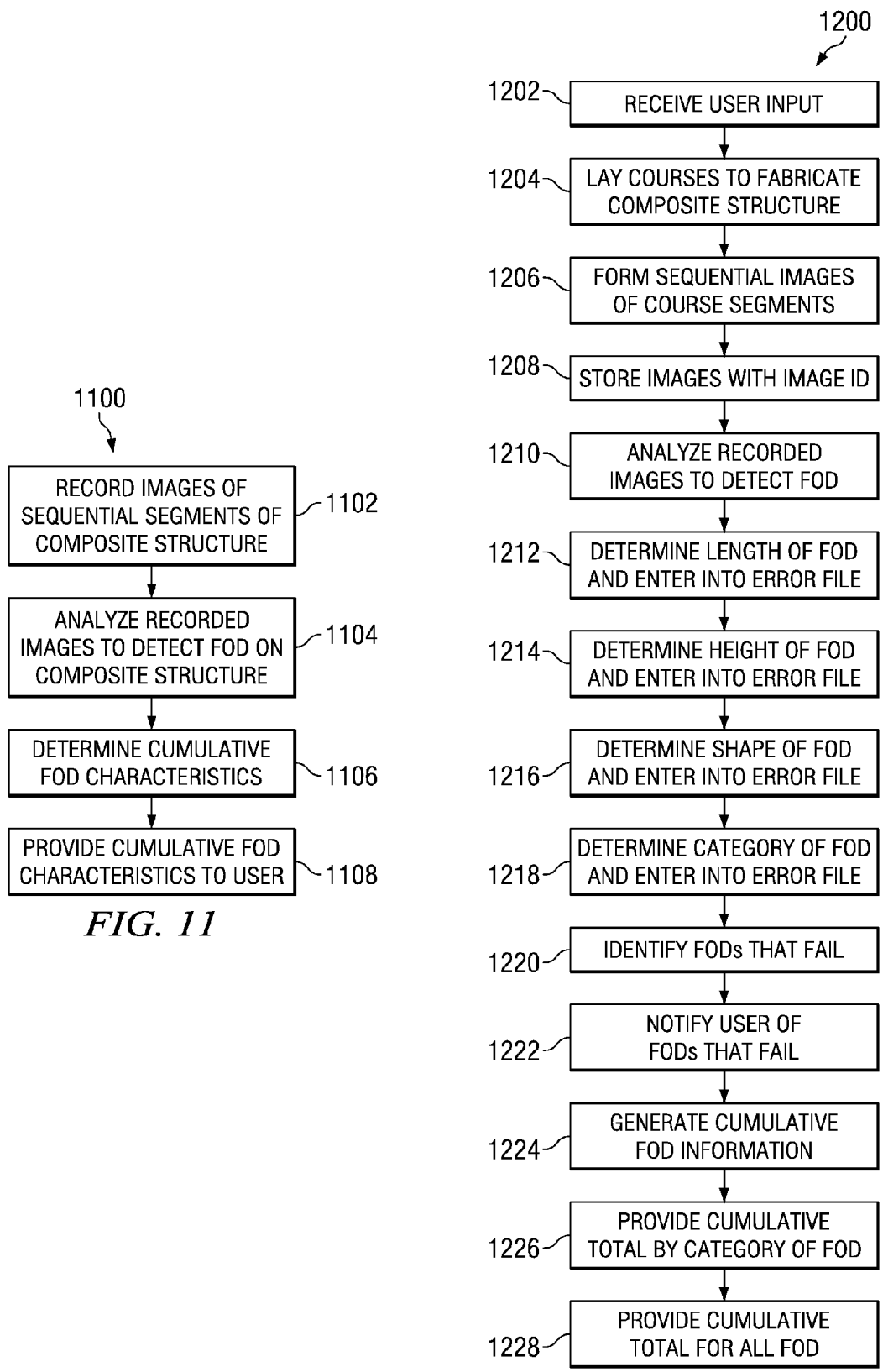

METHOD AND SYSTEM FOR DETERMINING CUMULATIVE FOREIGN OBJECT CHARACTERISTICS DURING FABRICATION OF A COMPOSITE STRUCTURE

REFERENCE TO RELATED APPLICATION

This application is a Continuation-in-Part of U.S. patent application Ser. No. 10/726,099 filed Dec. 2, 2003 now U.S. Pat. No. 7,289,656.

BACKGROUND INFORMATION

1. Field

The present disclosure relates generally to the fabrication of composite structures and, more particularly, to a method and system for determining cumulative foreign object characteristics during fabrication of a composite structure.

2. Background

Composite structures for aircraft and other applications have been known for many years and can be fabricated in many different ways. One advantageous technique for fabricating composite structures is a fiber and tape placement process. According to conventional techniques, one or more ribbons of a composite resin material, also known as composite strands or tows, are laid down on a substrate by a material placement machine. The substrate may be a tool or mandrel, but may also be one or more underlying layers of composite material that have been previously laid down and compacted.

Conventional placement processes utilize a heat source in conjunction with a compaction roller to apply the ribbon or tow onto the substrate at the nip of the compaction roller. More particularly, the ribbon or tow of composite resin material and the underlying substrate are heated at the nip as the material placement machine moves across the substrate to increase the tackiness of the resin material while the resin material is being subjected to compressive force by the compaction roller to adhere a strip or course of the composite resin material to the substrate.

To form a composite structure, a plurality of courses of the composite material are laid down in a side-by-side manner to form a first layer or ply of composite material. A similar plurality of courses of composite material may then be applied to the surface of the first ply to form a second ply on the first ply. The process is repeated until a desired number of plies have been formed one above another. In this way, a composite structure can be fabricated course-by-course and ply-by-ply until the composite structure is completed.

As the courses of composite material are laid down by the material placement machine, foreign objects and debris (FOD) may accumulate on the surface of the composite structure. FOD may include, for example and without limitation, resin balls, fiber wads, and pieces of backing material.

When FOD occurs during the laying down of a course, it is desirable that the FOD be detected and removed from the surface of the ply being formed before the next ply is formed as the FOD will otherwise become embedded between adjacent plies which may be undesirable. Failure to remove FOD may also result in bulges and other inconsistencies in the final composite structure. It is desirable therefore, to be able to detect the presence of FOD in real time while the courses are being laid down to form a ply so that they may be removed before a subsequent ply is formed.

There are current systems that are able to detect discrete foreign object occurrences so that they may be removed. It would be desirable, however, to also make cumulative determinations with respect to the detection of FOD. For example and without limitation, it would be desirable to make cumulative determinations with respect to the total number of FOD detected during fabrication of a composite structure or with respect to the total number of each of various types of FOD that are detected during fabrication of the structure. Such information may be useful in identifying problem areas with regard to the material placement machine or the overall composite structure fabrication process to enable appropriate adjustments or changes to be made to reduce the occurrence of such foreign objects and for other reasons.

SUMMARY

An embodiment of the disclosure provides a method for determining cumulative foreign object characteristics during fabrication of a composite structure. Images of sequential segments of a composite structure may be recorded during placement of the composite structure. The recorded images may be analyzed for detecting foreign objects on the composite structure. Cumulative foreign object characteristics of the foreign objects detected on the composite structure may be determined, and the cumulative foreign object characteristics may be provided to a user.

A further embodiment of the disclosure provides a system for determining cumulative foreign object characteristics during fabrication of a composite structure. The system may include a vision system for recording images of sequential segments of a composite structure during placement of the composite structure, and
a processor for analyzing the recorded images for detecting foreign objects on the composite structure, and for determining cumulative foreign object characteristics of the foreign objects detected on the composite structure. The system may also include an output for providing the cumulative foreign object characteristics to a user.

A further embodiment of the disclosure provides a method for determining cumulative foreign object characteristics during fabrication of a composite structure. Images of sequential segments of a course of a ply of a composite structure being fabricated may be recorded during placement of the course. Each recorded image may be analyzed for determining dimensional attributes of each foreign object detected on each segment of the course. A type of each foreign object detected on each segment of the course may be identified from the determined dimensional attributes, and cumulative foreign object characteristics for each identified type of foreign object may be determined. The cumulative foreign object characteristics may be provided to a user.

A further embodiment of the disclosure provides a method for determining cumulative foreign object characteristics for foreign objects accumulating on a composite structure during fabrication of the composite structure by a fiber and tape placement process. User input information regarding parameters to be used in generating the cumulative foreign object characteristics may be received. Images of sequential segments of the composite structure during placement of the composite structure may be recorded, and each recorded image may be stored with an identification of each recorded image. Each recorded image may be analyzed for determining dimensional attributes of each foreign object detected on the sequential segments of the composite structure, and a type of each foreign object detected on the sequential segments may be identified from the determined dimensional attributes, wherein the type of each foreign object comprises one of a resin ball, a fiber wad and a piece of backing material. Cumulative foreign object characteristics for the identified foreign objects may be determined, wherein the cumulative foreign object characteristics comprises at least one of a cumulative total of foreign objects detected, and a cumulative total for each type of foreign object detected, and the determined cumulative foreign object characteristics may be provided to the user.

A further embodiment of the disclosure provides a system for determining cumulative foreign object characteristics for foreign objects accumulating on a composite structure during fabrication of the composite structure by a fiber and tape placement process. The system may include a user input for receiving user input information regarding parameters to be used in generating the cumulative foreign object characteristics. The system may also include a vision system for recording images of sequential segments of the composite structure during placement of the composite structure, and a memory for storing each recorded image with an identification of each recorded image. The system may also include a processor for analyzing each recorded image for determining dimensional attributes of each foreign object detected on the sequential segments of the composite structure, for identifying a type of each foreign object detected on the sequential segments from the determined dimensional attributes, wherein the type of each foreign object comprises one of a resin ball, a fiber wad and a piece of backing material, and for determining cumulative foreign object characteristics for the identified foreign objects, wherein the cumulative foreign object characteristics comprises at least one of a cumulative total of foreign objects detected and a cumulative total for each type of foreign object detected. A display may provide the determined cumulative foreign object characteristics to the user.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

FIG. 11 is an illustration of a flowchart of a method for determining cumulative foreign object characteristics of a composite structure according to an advantageous embodiment of the disclosure; and FIG. 12 is an illustration of a flowchart of a method for determining cumulative foreign object characteristics of a composite structure according to a further advantageous embodiment of the disclosure.

DETAILED DESCRIPTION

Figure 1:
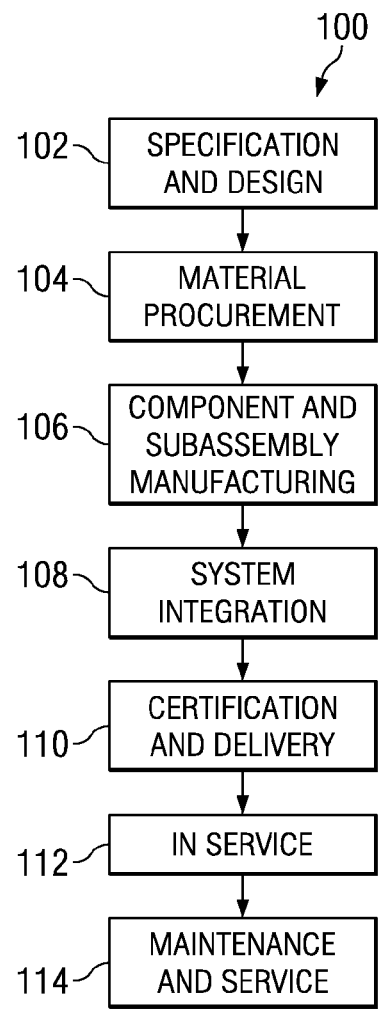
FIG. 1 is a diagram illustrating an aircraft manufacturing and service method in which an advantageous embodiment may be implemented.
Figure 2:
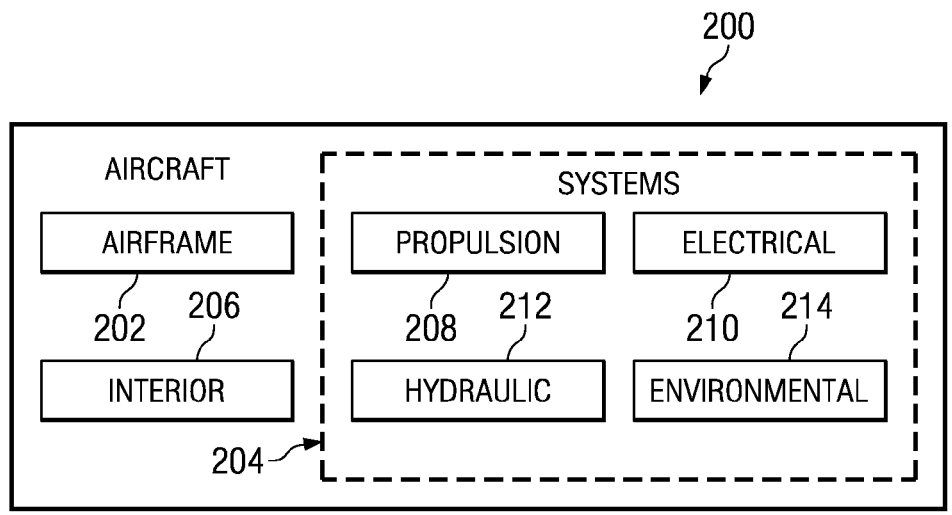
FIG. 2 is a diagram of an aircraft in accordance with an advantageous embodiment.

Referring more particularly to the drawings, embodiments of the disclosure may be described in the context of the aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104. During production, part and sub-assembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automobile industry and the boat and ship building industry.

Apparatus and methods embodied herein may be employed during any one or more of the stages of aircraft manufacturing and service method 100 in FIG. 1. For example, parts or subassemblies produced in part and subassembly manufacturing 106 in FIG. 1 may be fabricated or manufactured in a manner similar to parts or subassemblies repaired or modified while aircraft 200 is in service 112 in FIG. 1.

Also, one or more apparatus embodiments, method embodiments, or a combination thereof may be utilized during production stages, such as part and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 in FIG. 1 or during maintenance and service 114 in FIG. 1. More specifically, the different advantageous embodiments may be used during maintenance and service 114 in FIG. 1 to provide ply lay-up data for use in maintenance operations, such as, for example, repair or modification of composite parts.

Figure 3:
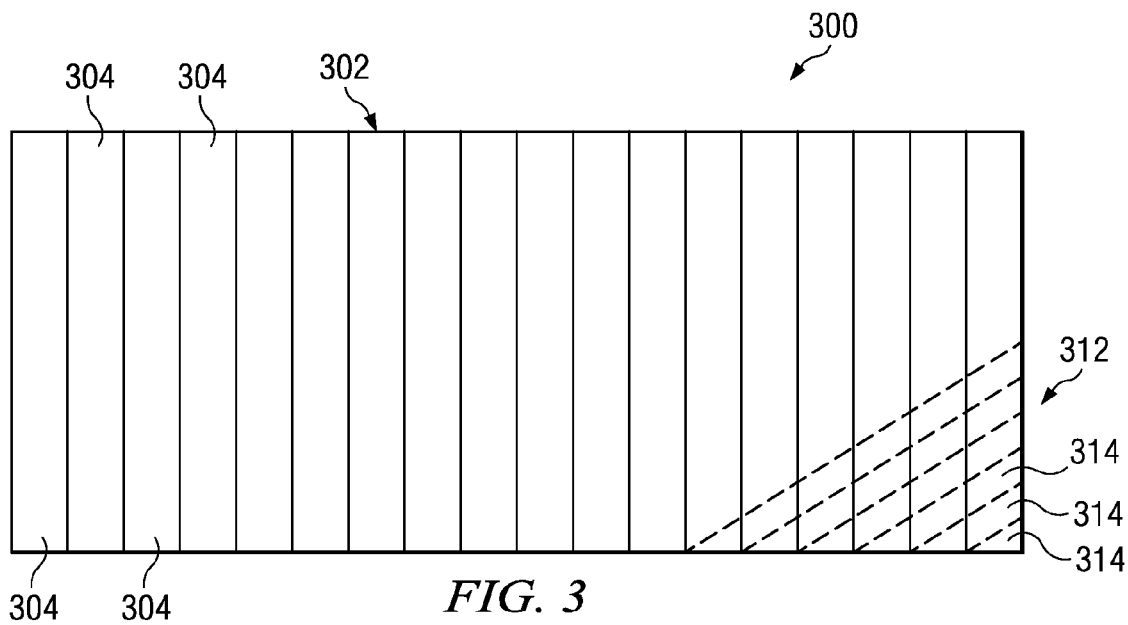
FIG. 3 is an illustration of a top view of a composite structure to assist in explaining advantageous embodiments of the disclosure.

FIG. 3 is an illustration of a top view of a composite structure to assist in explaining advantageous embodiments of the disclosure. The composite structure is designated by reference number 300, and is generally composed of a plurality of layers or plies of composite material formed one on top of another, with each ply being formed of a plurality of strips or courses of composite material arranged side-by-side.

More particularly, FIG. 3 illustrates a top ply 302 of composite structure 300 formed of a plurality of courses 304 of composite material arranged side-by-side. As shown in FIG. 3, top ply 302 is formed of eighteen courses 304. This is intended to be exemplary only as the plies of composite structure 300 can be formed of any desired number of courses to fabricate a composite structure of any desired size.

As indicated above, composite structure 300 may comprise a plurality of plies, with each ply being formed of a plurality of courses arranged side-by-side. The courses of adjacent plies may be oriented at different angles. FIG. 3 illustrates, in dashed line, a portion of a second ply 312 directly beneath ply 302 and formed of side-by-side courses 314 that are oriented at 45 degrees relative to courses 304 of ply 302.

A composite structure such as composite structure 300 may, for example and without limitation, be composed of six plies, with two of the plies having courses that are oriented horizontally, two of the plies having courses oriented at +45 degrees with respect to the horizontal courses, and two of the plies having courses oriented at −45 degrees with respect to the horizontal courses.

Courses 304 may comprise a composite resin material, for example and without limitation, a Hercules 3501-6 resin, having a plurality of fibers, for example and without limitation, carbon fibers, embedded therein. As will be explained more fully hereinafter, courses 304 may be laid down one at a time by a material placement machine (not shown in FIG. 3) that applies heat to soften the resin material, and a compaction force to adhere the courses to a substrate as the material placement machine passes back and forth over the substrate. The substrate may be a mandrel or other structure with respect to the first ply that is laid down, and an underlying ply or plies for subsequent plies that are laid down.

During the process of laying down the courses side-by-side to form a ply of a composite structure, various types of foreign objects and debris (FOD) may accumulate on the surface of the ply being formed. Such foreign objects and debris, also known as foreign object debris, and often referred to herein simply as "foreign objects" may include, for example and without limitation, resin balls, fiber wads and pieces of backing material.

Figure 4:
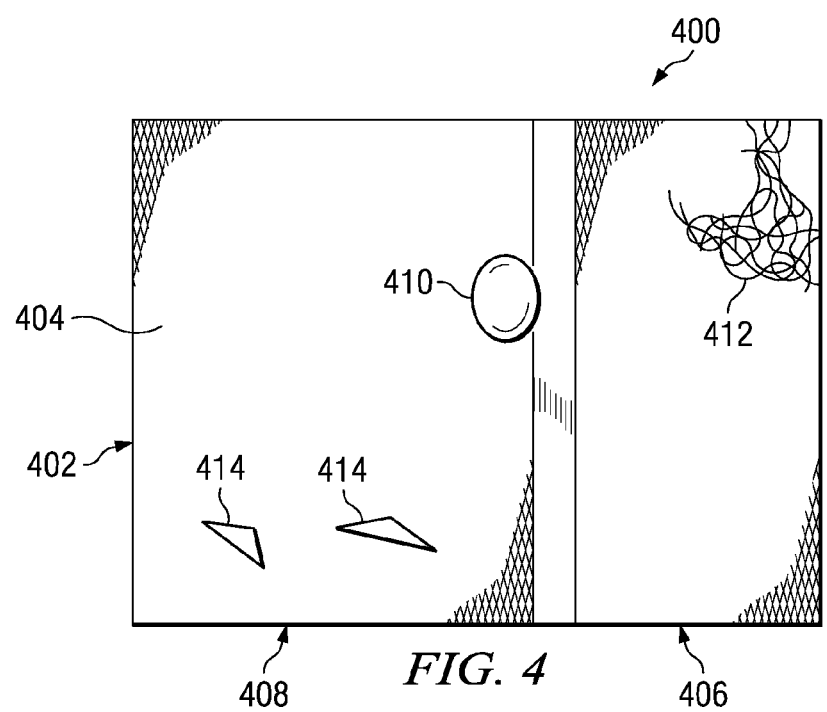
FIG. 4 is an illustration of a portion of a composite structure showing foreign objects that have accumulated on a surface of the composite structure to assist in explaining advantageous embodiments of the disclosure.

FIG. 4 is an illustration of a portion of a composite structure showing foreign objects that have accumulated on a surface of the composite structure to assist in explaining advantageous embodiments of the disclosure. In particular, FIG. 4 illustrates a surface 404 of a portion of a ply 402 of a composite structure 400. The illustrated portion of ply 402 includes portions of side-by-side courses 406 and 408.

FIG. 4 also illustrates several foreign objects that have accumulated on surface 404 of ply 402. The foreign objects illustrated include resin ball 410, fiber wad 412 and several pieces of backing material 414.

Resin balls form as a result of the composite resin material of which the courses are formed being only partially cured and gummy as a course is laid down to form the composite structure. Resin can collect on the material placement machine and periodically drop off of the machine onto a ply as a course is being laid down forming a resin ball such as resin ball 410 on the surface of the ply being formed. A resin ball may comprise a relatively small, generally spherical-shaped object having a size of, for example, about one-sixteenth inch in diameter. Resin balls typically accumulate near a side edge of a course or between adjacent courses as shown in FIG. 4.

Fiber wads 412, also referred to as fuzz balls, comprise an accumulation of loose fibers that separate from the composite resin material as a course is being laid down. Fiber wads 412 tend to be irregular in shape and are usually larger than resin balls, for example, about one-quarter inch or more across.

Pieces of backing material 414, formed, for example, of Mylar or paper, may also fall onto and stick to the surface of a course being laid down in a material placement operation in which the courses are applied from a spool carrying a continuous length of tape containing a backing material which must be removed before the courses are laid down. Pieces of backing material 414 tend to be of a regular, generally triangular shape and may have dimensions of from about one-half inch by about one-sixteenth inch.

The presence of foreign objects, such as resin ball 410, fiber wad 412 and pieces of backing material 414 on the surface of a ply of a composite structure being formed may be undesirable for several reasons. For example, the foreign objects may become entrapped between plies of the composite structure being formed which may be undesirable. Also, the foreign objects may form lumps in the composite structure affecting the uniformity of the structure. It is, accordingly, desirable to detect foreign objects as they accumulate on the surface of a ply as the ply is being formed. By detecting foreign objects as the ply is being formed, the foreign objects may be removed before a subsequent ply is formed on top of the ply currently being formed.

It is also desirable to be able to identify the type of each foreign object that is detected and to determine cumulative foreign object characteristics. For example and not by limitation, it is desirable to be able to determine a total number of foreign objects detected or a total number of each different type of foreign object detected. In general, determining foreign object characteristics may help recognize and correct problems in the material placement machine or in the overall material placement process to, for example and without limitation, reduce the number of occurrences of foreign objects.

Because, as shown in FIG. 4, different types of foreign objects are visually distinguishable from one another due to differences, for example, in size and shape, advantageous embodiments of the disclosure provide a method and system for detecting and categorizing foreign objects and for providing a cumulative record of detected foreign objects.

Figure 5:
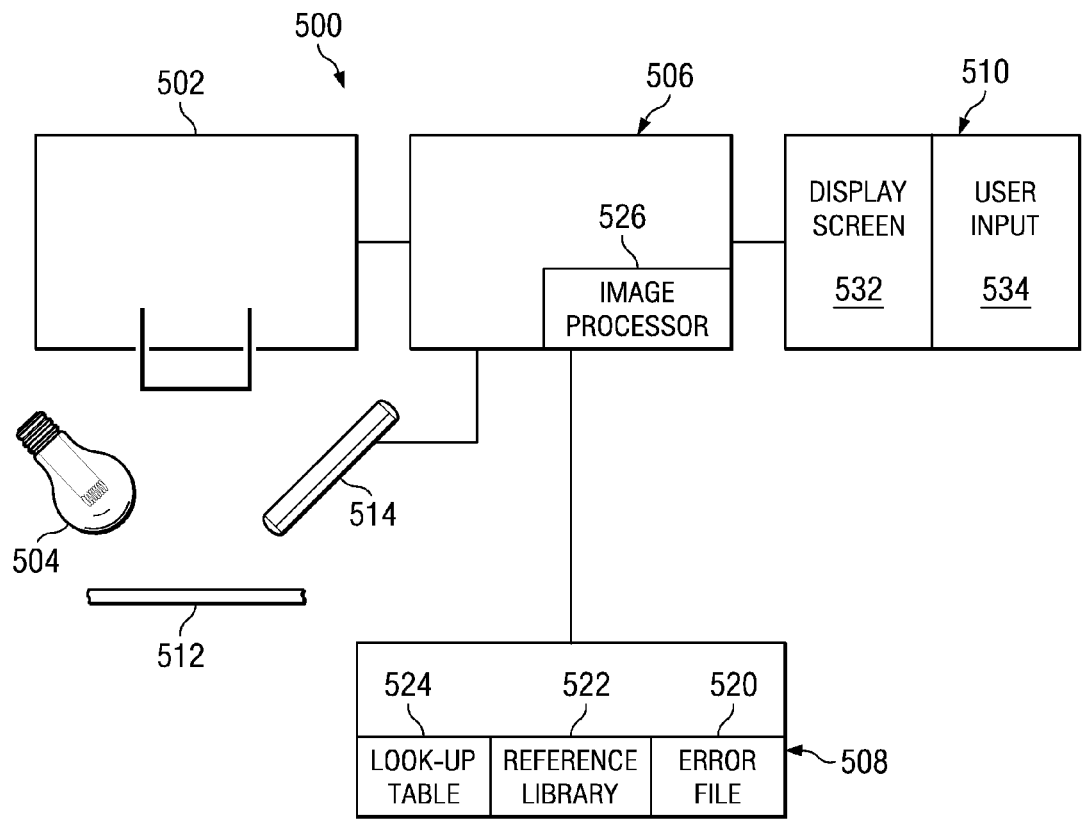
FIG. 5 is an illustration of a block diagram of a system for determining cumulative foreign object characteristics of a composite structure according to an advantageous embodiment of the disclosure.

FIG. 5 is an illustration of a block diagram of a system for determining cumulative foreign object characteristics of a composite structure according to an advantageous embodiment of the disclosure. The system is generally designated by reference number 500, and may include vision system 502, illumination system 504, processor 506, data storage unit 508 and user interface 510.

Vision system 502 may comprise one or more cameras positioned with respect to a course of composite material 512 being laid down so as to capture images of sequential segments of the course as the course is being laid down. Vision system 502 may be positioned immediately downstream of the nip of a compaction roller of a material placement machine at which a course is heated and adhered to an underlying substrate such as an underlying ply of a composite structure being formed.

Illumination system 504 may comprise one or more light sources positioned to illuminate the segment of the course being imaged by vision system 502. The light from illumination system 504 will be reflected differently by foreign objects on the segment being illuminated than by the composite material of the segment itself, enabling vision system 502 to capture visible images of foreign objects on the segment.

A wide range of cameras can be used according to advantageous embodiments of the disclosure. Such cameras may include, for example and without limitation, commercially-available cameras capable of capturing color or black and white images. Vision system 502 may also comprise a television or other type of video camera having an image sensor and a lens through which light passes when the camera is in operation. Vision system 502 may also include an infrared-sensitive camera, a visible light camera with infrared-pass filtration, a fiber optic camera, a coaxial camera, a Charge Coupled Device (CCD), or a Complementary Metal Oxide Sensor (CMOS).

Illumination system 504 may include one or more light sources of the same or different type. Illumination system 504 may include, for example and without limitation, one or more infrared light sources, and/or one or more fluorescent light sources, stroboscopic light sources, noble gas arc lamp light source, laser sources, or light emitting diode (LED) sources.

Illumination system 504 may be operated at a power level that increases the infrared (IR) component of the light which works well for inspecting dark course materials, such as carbon. In general, however, the particular power levels and wavelengths for the illumination system may depend, at least in part, on the speed and sensitivity of the vision system, the speed at which the courses are being laid, and the reflectivity of the material of the courses being laid.

Figure 6:
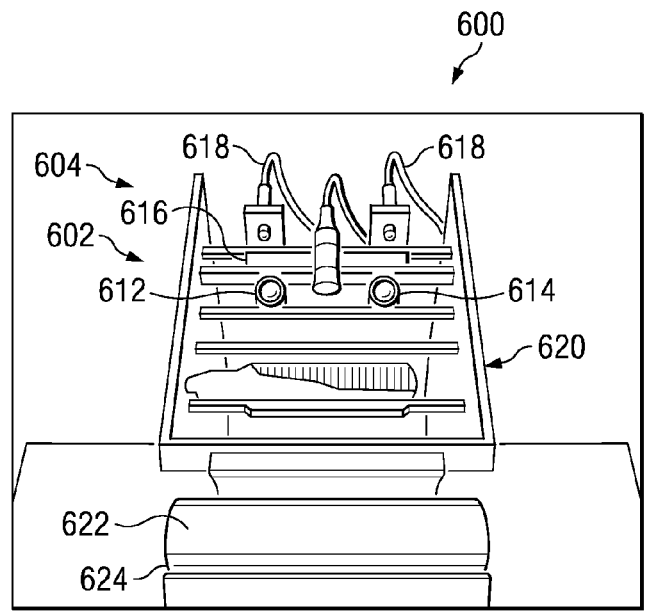
FIG. 6 is an illustration of a front view of a head unit of a material placement machine having a vision system and an illumination system mounted thereon according to an advantageous embodiment of the disclosure.

FIG. 6 is an illustration of a front view of a head unit of a material placement machine having a vision system and an illumination system mounted thereon according to an advantageous embodiment of the disclosure. The material placement machine is generally designated by reference number 600, and includes vision system 602 and illumination system 604 mounted thereon. Vision system 602 may be implemented as vision system 502 in FIG. 5, and illumination system 604 may be implemented as illumination system 504 in FIG. 5.

In the advantageous embodiment illustrated in FIG. 6, vision system 602 includes two cameras 612 and 614. As will be explained more fully hereinafter, cameras 612 and 614 may be utilized when the courses being laid down have a width of 8 inches such that each camera will form an image of a three-inch by four-inch portion of a three inch by eight inch segment of a course. In advantageous embodiments of the disclosure in which courses laid down may be 4 inches wide, a single camera may be sufficient.

Illumination system 604 may also include a pair of light sources 616 and 618. Light source 616 may be a light source that illuminates an area being imaged, such as a three inch by four inch segment of a four inch wide course, or a three inch by eight inch segment of an eight inch wide course. In the advantageous embodiment illustrated in FIG. 6, area light source 616 may comprise a visible light source.

Light source 618 may comprise a plurality of small, solid state lasers to form a plurality of thin laser lines on a course segment being imaged. In this regard, it has been found that the different light sources may facilitate detecting and identifying different types of foreign objects on the surface of a course.

Figure 7:
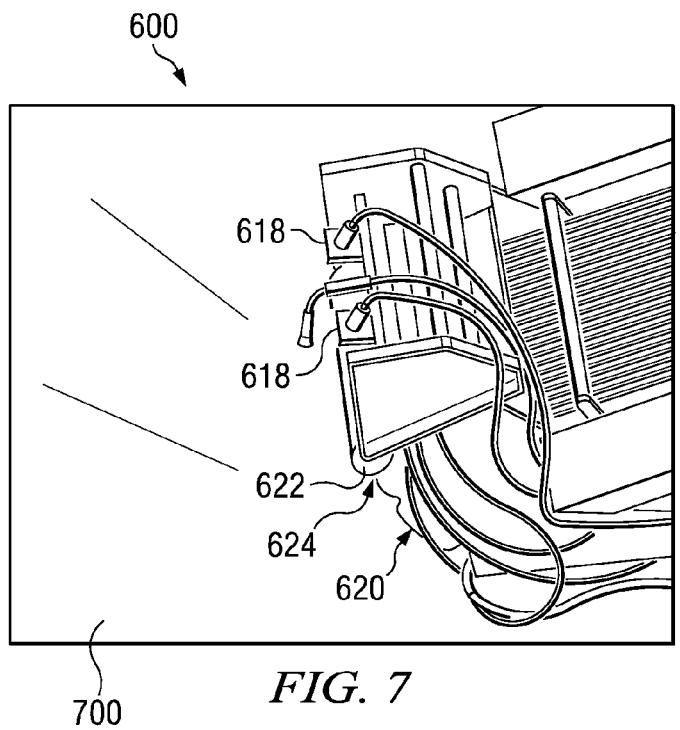
FIG. 7 is an illustration of the head unit of FIG. 6 properly positioned with respect to the surface of a composite structure being fabricated.

FIG. 7 is an illustration of the head unit of FIG. 6 properly positioned with respect to the surface of a composite structure being fabricated. More particularly, FIG. 7 illustrates head unit 620 positioned to lay down a course of composite material to form a ply of a composite structure, generally designated by reference number 700. As shown, in FIG. 7, laser light sources 618 are mounted on head unit 620 so as to be closely spaced to the surface of the composite structure being formed, and light source 616 and cameras 612 and 614, although not visible in FIG. 7, are also mounted to be close to the surface of the composite structure.

Returning to FIG. 5, vision system 502 is adapted to capture real-time images of sequential segments of course 512 as the head unit 620 of material placement machine 600 shown in FIGS. 6 and 7 moves back and forth across the composite structure. The segment or inspection area at which the images are captured may be just downstream of the nip 624 of the compaction roller 622 of machine 600 as shown in FIGS. 6 and 7.

Captured images may be stored in a memory unit 508 for immediate analysis and/or processing by processor 506. Processor 506 may receive the images directly from vision system 502 or from memory unit 508 in which the images have been stored. Processor 506 may then process and analyze the images to detect and identify foreign objects captured by the images and to determine cumulative foreign object characteristics from the detected and identified foreign objects. Processor 506 and memory unit 508 may be components of a conventional computer.

As will be explained more fully hereinafter, memory unit 508 may include an error file 520, an image processing reference library 522 and a look-up table 524 which are used by processor 506 to identify foreign objects captured by the images and to determine cumulative foreign object characteristics. The processor 506 may include image processing software 526 to identify the different types of foreign objects captured on the images of the courses.

User interface 510 is in communication with processor 506. As shown in FIG. 5, user interface 510 may include a display screen 532 such as, without limitation, on a computer monitor, and may also include a user input 534 such as, without limitation, a keyboard and/or a mouse for moving a cursor to permit a user to input various system settings and parameters.

Figure 10:
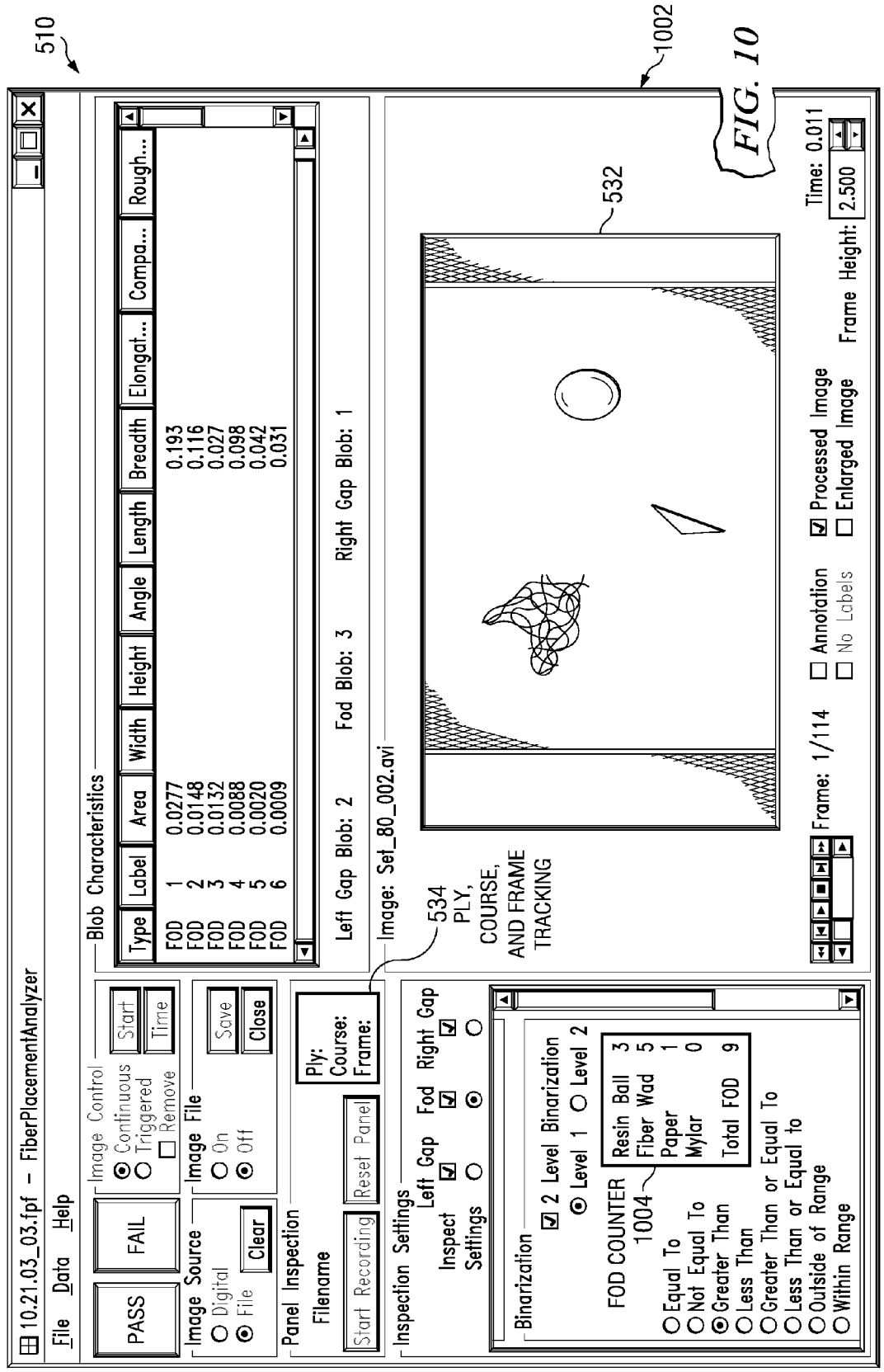
FIG. 10 is an illustration of the user interface in the system for determining cumulative foreign object characteristics of a composite structure of FIG. 5.

Display screen 532 may comprise a window, illustrated in FIG. 10, in which images of segments of the composite structure 512 may be displayed for viewing by the user.

System 500 may also include a marking device 514 for marking the location of foreign objects on the composite structure 512. The marking device 514 may be triggered by processor 506 when a foreign object is detected. The marking device 506 may spray or otherwise deposit an amount of ink, paint or the like onto the composite structure 512 in those areas where foreign objects have been detected. The markings enable the location of the foreign objects to be readily identified to facilitate removal of the foreign objects.

In operation of system 500 in accordance with advantageous embodiments of the disclosure, vision system 502 produces images of a course as it is being laid down by material placement machine 600 (FIGS. 6 and 7). Each image may have a width equal to the width of the course, for example and without limitation, four inches or eight inches, and each image may be of the same height, for example and without limitation, three inches, to provide a mechanism for establishing the location of foreign objects that are detected.

Software in processor 506 records the ply number and course number into error log 520 of memory unit 508 according to the expected number of plies and courses per ply that were entered by a user via user input 534 of user interface 510. Each time the head unit 620 of material placement machine 600 lifts up from the surface of the composite structure at the end of a pass, it signals the end of one course and the beginning of the next course such that the courses may be identified by the processor. Each image is also assigned a sequential number by the processor 506 and the number is logged into the error file 520 along with the ply number and the course number of the course segment of which the image was taken.

Figure 8:
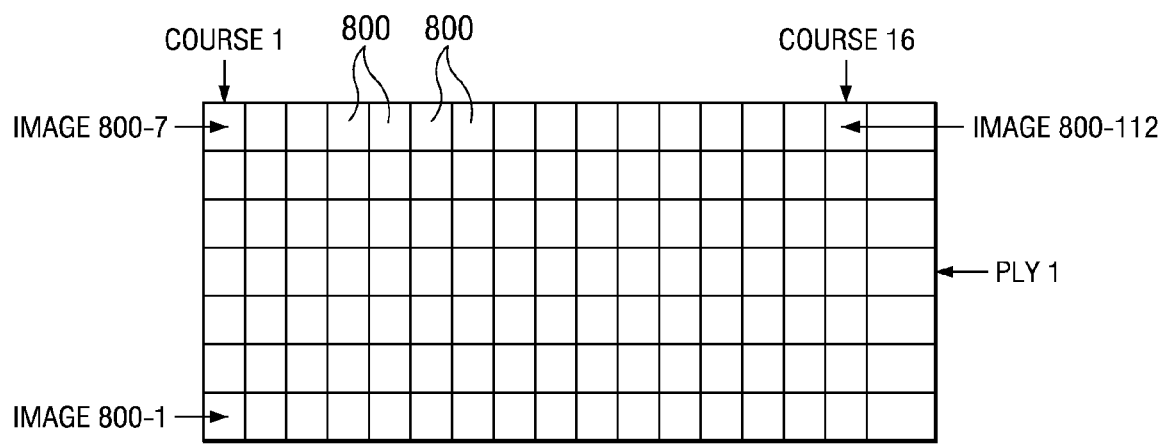
FIG. 8 is an illustration showing a layout of courses and images of segments of the courses forming a ply of a composite structure according to an advantageous embodiment of the disclosure.

FIG. 8 is an illustration showing a layout of courses and images of segments of the courses forming a ply of a composite structure according to an advantageous embodiment of the disclosure. FIG. 8 shows the individual images, generally designated as images 800, that were taken of segments of courses forming a ply, designated as ply 1 in FIG. 8, as the courses were laid down beginning with image 800-1 at the bottom of course 1 to image 800-7 at the top of course 1, and ending with image 800-112 at the top of course 16. If a foreign object such as one or more of foreign objects 410, 412 or 414, from FIG. 4 appears in one of the images 800, its dimensional attributes (e.g., dimensional attributes 902 illustrated in FIG. 9) are determined by the image processing software 526 in FIG. 5 and entered into error file 520 together with the image number, the course number and the ply number. The image processing software may use standard image processing routines such as edge detection to determine the dimensional attributes 902 of detected foreign objects 410, 412, 414 in FIG. 4.

Once the dimensional attributes 902, for example and without limitation, the length, height and shape, of a detected foreign object have been determined, the dimensional attributes are used in conjunction with image processing reference library 522 of "blob" options and in conjunction with look-up table 524 to assign a type or category 906 to the detected foreign object 410, 412, 414. This same look up table 524 may provide maximum allowable sizes for each category or type 906 of foreign object 410, 412, 416, on which to base acceptance or rejection of the foreign object.

Figure 9:
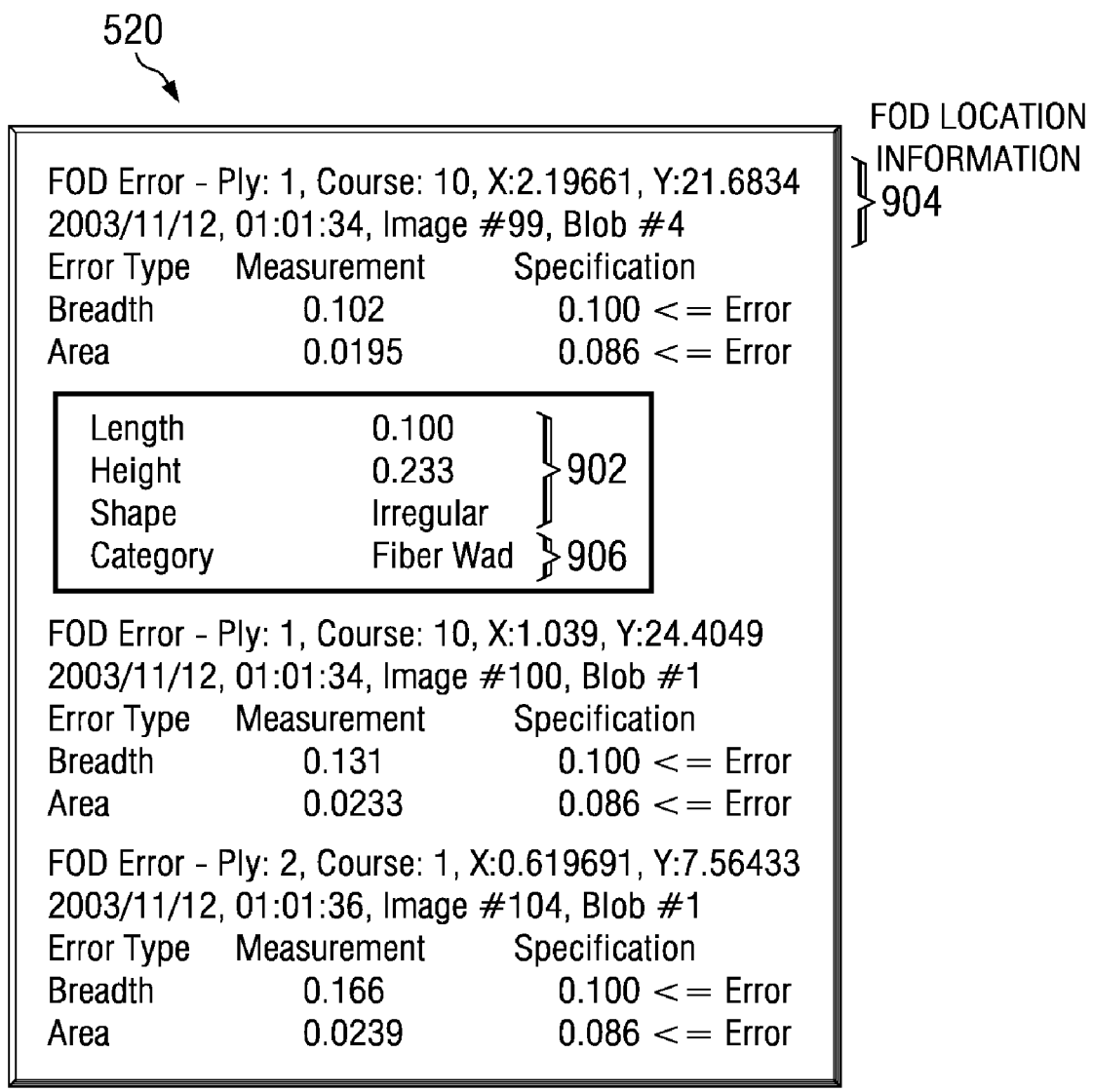
FIG. 9 is an illustration schematically showing a segment of the error file in the processor of the system for determining cumulative foreign object characteristics of a composite structure of FIG. 5.

FIG. 9 is an illustration schematically showing a segment of the error file in the processor of the system for determining cumulative foreign object characteristics of a composite structure of FIG. 5. In particular, FIG. 9 shows a segment of error table 520 along with added attributes 902 and categorization 906. As shown at 904, the file notes the x-y position of the foreign object based on uniform width (x) and the set image frame size (y). Cumulative FOD per unit area can be extracted from the known dimensional information and from the detected FOD numbers.

FIG. 10 is an illustration of the user interface in the system for determining cumulative foreign object characteristics of a composite structure of FIG. 5. As shown in FIG. 10, user interface 520 includes display screen 532 that displays a current segment or inspection area being imaged in real time. User inputs 534 are provided for entering and changing parameters such as acceptance criteria and image frame size. A highly visible red-green "pass/fail" indicator 1002 may be provided to flash in real-time as foreign objects 410, 412, 414 from FIG. 4 are detected and measured. FOD counter 1004 may provide a running total by category and cumulative total for FOD.

FIG. 11 is an illustration of a flowchart of a method for determining cumulative foreign object characteristics of a composite structure according to an advantageous embodiment of the disclosure. More particularly, FIG. 11 illustrates a method for determining cumulative foreign object characteristics for foreign objects accumulating on a composite structure during fabrication of the composite structure by a fiber and tape placement process according to an advantageous embodiment of the disclosure.

The method is generally designated by reference number 1100 and begins by recording images of sequential segments of a composite structure during placement of the composite structure (Step 1102). The recorded images are then analyzed for detecting foreign objects on the composite structure (Step 1104), and cumulative foreign object characteristics of the foreign objects detected on the composite structure are determined (Step 1106). The cumulative foreign object characteristics are then provided to a user (Step 1108).

FIG. 12 is an illustration of a flowchart of a method for determining cumulative foreign object characteristics of a composite structure according to a further advantageous embodiment of the disclosure. More particularly, FIG. 12 illustrates a method for determining cumulative foreign object characteristics for foreign objects accumulating on a composite structure during fabrication of the composite structure by a fiber and tape placement process according to a further advantageous embodiment of the disclosure.

The method is generally designated by reference number 1200 and begins by receiving user input (Step 1202). The user input, which may be implemented as user input 534 in FIG. 5, may include information regarding the composite structure to be fabricated, and information regarding parameters to be used in generating the cumulative information. For example and without limitation, the user input regarding the composite structure to be fabricated may include information regarding the number of plies and the number of courses of each ply of the composite structure being fabricated. The information regarding the parameters for generating the cumulative information may include image frame size and acceptance criteria for accepting or rejecting an identified foreign object, such as one of foreign objects 410, 412 and 414 in FIG. 4.

After the input information has been received, a material placement machine begins laying down courses to fabricate the composite structure course-by-course and ply-by-ply (Step 1204). As the courses are being laid down, images of sequential segments of the courses are formed in real time (Step 1206). In an advantageous embodiment of the disclosure, the width of each image may be, for example and without limitation, equal to the width of the course being placed, and the length of each image along the course may be, for example and without limitation, the same. For example and without limitation, in an advantageous embodiment wherein the width of the course being placed is four inches, the length of each image may be three inches to form images of three inch by four inch rectangular sequential segments of a course. In an advantageous embodiment wherein the width of the course being placed is eight inches, each sequential image may be formed of a pair of side-by-side images sections, each section being a three inch by four inch rectangle to form images of three inch by eight inch sequential segments of the course.

As the images of the sequential course segments are formed, each image is logged into an error file, which may be error file 520 in FIG. 5, together with an identification of the image (Step 1208). More particularly, each image is assigned a sequential image number by inspection software, and, in addition, the software records the ply number and the course number of the course segment that was imaged according to the information entered by the user in Step 1202. Thus, the course segment represented by each image is identified and stored with its associated image in the error file.

Each image is then analyzed to detect any foreign objects (FOD), for example and without limitation, one of foreign objects 410, 412 or 414, on course segments corresponding to the images (Step 1210) and dimensional attributes, for example and without limitation, the length (Step 1212), the height (Step 1214) and the shape (Step 1216), of the foreign object are determined and entered into the error file 520 as shown at 902 in FIG. 9. The determined attributes are then analyzed using an image processing reference library of "blob" options in conjunction with a look-up table 524 in order to determine a type or category of the detected foreign object, and the category is also entered into error file 520 as shown at 906 in FIG. 9 (Step 1218).

The look-up table 524 may also provide maximum allowable sizes for each category or type of FOD such that software can identify FODs that fail (Step 1220). When FOD is rejected, the user is notified, for example, by actuating indicator 1002 on user interface 510 illustrated in FIG. 5 (Step 1222). The indicator 1002 operates in real time as foreign objects are detected and measured so that the user may take appropriate action to remove a foreign object before the next ply is applied over the current ply being formed.

The software also generates cumulative information regarding detected and identified FOD (Step 1224). This cumulative information may also be provided to the user, for example, as a cumulative total by category of FOD (Step 1226) and/or as a cumulative total for all FOD (Step 1228). Such cumulative information may include cumulative FOD information per unit area determined using the known dimensional information and FOD identification numbers, or the information may include cumulative FOD information per composite unit fabricated or cumulative information on another basis.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for determining cumulative foreign object characteristics during fabrication of a composite structure, comprising:
   recording, in a data storage unit, images of sequential segments of a composite structure during placement of the composite structure such that recorded images are formed;
   analyzing, by a processor which receives the recorded images from the data storage unit, the recorded images for detecting foreign objects on the composite structure, and analyzing includes:
      analyzing each of the recorded images for determining dimensional attributes of each foreign object detected on the composite structure; and
      identifying a type of each foreign object detected on the composite structure from the determined dimensional attributes;
   determining, by the processor, cumulative foreign object characteristics of the foreign objects detected on the composite structure; and
   storing the cumulative foreign object characteristics.

2. The method of claim 1, wherein analyzing each of the recorded images for determining dimensional attributes of each foreign object detected on the composite structure, comprises:
   analyzing each of the recorded images for determining a length, a height and a shape of each foreign object detected on the composite structure.

3. The method of claim 1, wherein determining cumulative foreign object characteristics of the foreign objects detected on the composite structure, comprises:
   determining a cumulative total of foreign objects detected on the composite structure.

4. The method of claim 3, wherein determining a cumulative total of foreign objects detected on the composite structure, comprises:
   determining a cumulative total of foreign objects detected per unit area on the composite structure.

5. The method of claim 1, wherein determining cumulative foreign object characteristics of the foreign objects detected on the composite structure, comprises:
   determining a cumulative total for each type of foreign object detected on the composite structure.

6. The method of claim 5, wherein determining a cumulative total for each type of foreign object detected on the composite structure, comprises:
   determining a cumulative total for each type of foreign object detected per unit area on the composite structure.

7. The method of claim 1, wherein determining cumulative foreign object characteristics of the foreign objects detected on the composite structure, comprises:
   maintaining a running count of foreign objects detected on the composite structure.

8. The method of claim 1, wherein the types of foreign objects include resin balls, fiber wads, and pieces of backing material.

9. The method of claim 1, wherein the sequential segments of a composite structure comprises sequential segments of a course of a ply of the composite structure.

10. A system for determining cumulative foreign object characteristics during fabrication of a composite structure, comprising:
    a vision system for recording images of sequential segments of a composite structure during placement of the composite structure such that recorded images are formed;
    a processor for analyzing the recorded images for detecting foreign objects on the composite structure, and for determining cumulative foreign object characteristics of the foreign objects detected on the composite structure;
    a data storage device for storing the cumulative foreign object characteristics;

an illumination system for illuminating the sequential segments of the composite structure being imaged, comprising:
  a visible light source for illuminating areas defined by the sequential segments; and
  a plurality of laser light sources for illuminating narrow strips of the sequential segments.

11. The system of claim 10, wherein the vision system comprises at least one camera.

12. The system of claim 10, wherein the processor analyzes the recorded images for detecting foreign objects on the composite structure by analyzing each of the recorded images for determining dimensional attributes of each foreign object detected on the composite structure, and by identifying a type of each foreign object detected on the composite structure from the determined dimensional attributes.

13. The system of claim 12, wherein the dimensional attributes of each foreign object comprise a length, a height and a shape of each foreign object.

14. The system of claim 12, wherein the cumulative foreign object characteristics of the foreign objects detected on the composite structure, comprises a cumulative total for each type of foreign object detected on the composite structure.

15. The system of claim 12, wherein the types of foreign objects include resin balls, fiber wads and pieces of backing material.

16. The system of claim 10, wherein the cumulative foreign object characteristics of the foreign objects detected on the composite structure, comprises a cumulative total of the foreign objects detected on the composite structure.

17. A method for determining cumulative foreign object characteristics during fabrication of a composite structure, comprising:
  recording, in a data storage unit, images of sequential segments of a course of a ply of a composite structure being fabricated during placement of the course such that a number of recorded images are formed;
  analyzing, by a processor which receives the number of images from the data storage unit, each of the number of recorded images for determining dimensional attributes of each foreign object detected on each segment of the course;
  identifying, by the processor, a type of each foreign object detected on each segment of the course from the determined dimensional attributes;
  determining, by the processor, cumulative foreign object characteristics for each identified type of foreign object; and
  storing the cumulative foreign object characteristics.

18. A method for determining cumulative foreign object characteristics for foreign objects accumulating on a composite structure during fabrication of the composite structure by a fiber and tape placement process, comprising:
  receiving, at a processor, user input information regarding parameters to be used in generating the cumulative foreign object characteristics;
  recording, in a data storage device, images of sequential segments of the composite structure during placement of the composite structure such that a number of recorded images are formed;
  storing, in the data storage device, each of the number of recorded images with an identification of each recorded image;
  analyzing, by the processor which receives the number of recorded images from the data storage device, each of the number of recorded images for determining dimensional attributes of each foreign object detected on the sequential segments of the composite structure;
  identifying, with the processor, a type of each foreign object detected on the sequential segments from the determined dimensional attributes, the type of each foreign object comprising one of a resin ball, a fiber wad and a piece of backing material, such that identified foreign objects are formed;
  determining, with the processor, cumulative foreign object characteristics for the identified foreign objects, the cumulative foreign object characteristics comprising at least one of a cumulative total of foreign objects detected, and a cumulative total for each type of foreign object detected; and
  storing the determined cumulative foreign object characteristics.

19. A system for determining cumulative foreign object characteristics for foreign objects accumulating on a composite structure during fabrication of the composite structure by a fiber and tape placement process, comprising:
  a user input for receiving user input information regarding parameters to be used in generating the cumulative foreign object characteristics;
  a vision system for recording images of sequential segments of the composite structure during placement of the composite structure;
  a memory for storing each recorded image with an identification of each recorded image;
  a processor for analyzing each recorded image for determining dimensional attributes of each foreign object detected on the sequential segments of the composite structure, for identifying a type of each foreign object detected on the sequential segments from the determined dimensional attributes, wherein the type of each foreign object comprises one of a resin ball, a fiber wad and a piece of backing material, and for determining cumulative foreign object characteristics for the identified foreign objects, wherein the cumulative foreign object characteristics comprises at least one of a cumulative total of foreign objects detected and a cumulative total for each type of foreign object detected; and
  a display for providing the determined cumulative foreign object characteristics to the user.

* * * * *